United States Patent [19]

Hübsch et al.

[11] Patent Number: 4,937,255

[45] Date of Patent: Jun. 26, 1990

[54] DISUBSTITUTED PYRROLES

[75] Inventors: Walter Hübsch; Rolf Angerbauer; Peter Fey; Hilmar Bischoff, all of Wuppertal; Dieter Petzinna, Duesseldorlf; Delf Schmidt, Wuppertal, all of Fed. Rep. of Germany; Günter Thomas, Arese, Italy

[73] Assignee: Bayer Aktiengesellschaft, Leverkusen, Fed. Rep. of Germany

[21] Appl. No.: 325,273

[22] Filed: Mar. 16, 1989

[30] Foreign Application Priority Data

Mar. 24, 1988 [DE] Fed. Rep. of Germany ....... 3809860
Oct. 3, 1988 [IT] Italy .................. 22158 A/88

[51] Int. Cl.$^5$ ............... A61K 31/40; C07D 207/337; C07D 401/04; C07D 401/14
[52] U.S. Cl. .................... 514/427; 514/248; 514/249; 514/252; 514/253; 514/256; 514/259; 514/269; 514/274; 514/307; 514/308; 514/309; 514/311; 514/312; 514/333; 514/338; 514/339; 514/341; 514/342; 514/343; 514/365; 514/367; 514/369; 514/372; 514/374; 514/375; 514/376; 514/378; 514/380; 514/387; 514/394; 514/395; 514/397; 514/414; 514/422; 544/235; 544/237; 544/238; 544/284; 544/295; 544/296; 544/310; 544/315; 544/316; 544/319; 544/333; 544/353; 544/354; 544/355; 544/356; 544/405; 546/140; 546/141; 546/142; 546/144; 546/145; 546/146; 546/147; 546/148; 546/152; 546/153; 546/155; 546/156; 546/157; 546/167; 546/170; 546/172; 546/173; 546/174; 546/176; 546/177; 546/256; 546/272; 546/273; 546/274; 546/280; 546/281; 548/152; 548/156; 548/157; 548/159; 548/170; 548/178; 548/180; 548/181; 548/182; 548/183; 548/187; 548/188; 548/189; 548/201; 548/204; 548/213; 548/214; 548/217; 548/220; 548/221; 548/224; 548/225; 548/226; 548/227; 548/228; 548/229; 548/230; 548/231; 548/232; 548/236; 548/243; 548/247; 548/248; 548/249; 548/305; 548/327; 548/328; 548/336; 548/455; 548/460; 548/461; 548/462; 548/465; 548/517; 548/518; 548/519; 548/521; 548/523; 548/524; 548/527; 548/561; 548/562; 548/532; 548/565

[58] Field of Search ............. 548/517, 561, 562, 152, 548/156-157, 159, 170, 178, 180-183, 187-189, 201, 204, 213-214, 217, 220-221, 224, 225-232, 236, 243, 247-249, 305, 327-328, 336, 455, 460-462, 465, 518-519, 521, 523, 524, 527; 514/248-249, 252-253, 256, 259, 269, 274, 307-309, 311-312, 333, 338-339, 341-343, 365, 367, 369, 372, 374-376, 378, 380, 387, 394-395, 397, 414, 422, 427; 544/235, 237-238, 284, 295-296, 310, 315, 316, 319, 333, 353-356, 405; 546/140-142, 144-148, 152-153, 155-157, 167, 170, 172-174, 176-177, 256, 272-274, 280, 281

[56] References Cited

FOREIGN PATENT DOCUMENTS 0221025 5/1989 European Pat. Off. .

Primary Examiner—Mark L. Berch
Attorney, Agent, or Firm—Sprung, Horn, Kramer & Woods

[57] ABSTRACT

For inhibiting 3-hydroxy-3-methylglutaryl coenzyme A and cholesterol biosynthesis, the novel disubstituted pyrroles of the formula

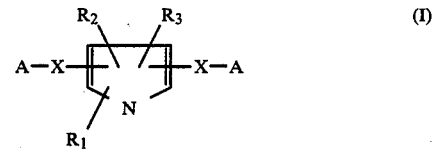

(I)

in which
$R^1$ is aryl or heteroaryl,
$R^2$ is cycloalkyl or optionally substituted alkyl,
$R^3$ is hydrogen or cycloalkyl, or optionally substituted alkyl, aryl or heteroaryl,
X is —CH$_2$—CH$_2$— or —CH=CH—,
A is

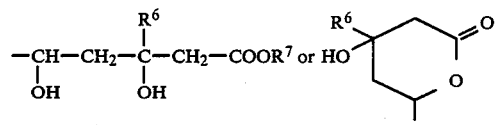

$R^6$ is hydrogen or alkyl, and
$R^7$ is hydrogen, a cation or alkyl, aryl or aralkyl.

10 Claims, No Drawings

DISUBSTITUTED PYRROLES

The invention relates to disubstituted pyrroles, intermediates for their preparation, their preparation and their use in medicaments.

It has been disclosed that lactone derivatives isolated from fungal cultures are inhibitors of 3-hydroxy-3-methyl-glutaryl coenzyme A reductase (HMG-CoA reductase) [mevinolin, EP-A No. 22,478; U.S. Pat. No. 4,231,938]. Moreover, certain indole derivatives or pyrazole derivatives are also inhibitors of HMG-CoA reductase [EP-A No. 1,114,027; U.S. Pat. No. 4,613,610].

Disubstituted pyrroles of the general formula (I)

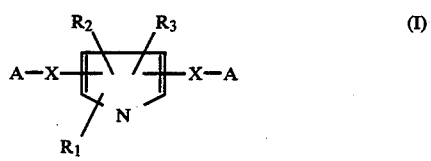

in which $R^1$
  denotes heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^4R^5$, each of which is identical or different,
wherein
  $R^4$ and $R^5$ are identical or different and
    denote alkyl, aryl, aralkyl, acyl, alkylsulphonyl or arylsulphonyl,
  or
    denotes aryl which can be monosubstituted to pentasubstituted by alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^4R^5$, each of which is identical or different,
wherein
  $R^4$ and $R^5$ have the abovementioned meaning,
$R^2$
  denotes cycloalkyl, or
  denotes alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl, or by a group of the formula —$NR^4R^5$,
wherein
  $R^4$ and $R^5$ are identical or different and
denote alkyl, aryl, aralkyl, acyl, alkylsulphonyl or arylsulphonyl, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals of the last mentioned substituents can be monosubstituted, disubstituted or trisubstituted by halogen, cyano, trifluoromethyl, trifluoromethoxy, alkyl, alkoxy, alkylthio or alkylsulphonyl, each of which is identical or different,
$R^3$
  denotes hydrogen, or
  denotes cycloalkyl, or
  denotes alkyl which can be substituted by halogen, cyano, alkoxy, alkylthio, alkylsulphonyl, trifluoromethyl, trifluoromethoxy, trifluoromethylthio, trifluoromethylsulphonyl, alkoxycarbonyl or acyl, or by a group of the formula —$NR^4R^5$,
wherein
  $R^4$ and $R^5$ have the abovementioned meaning, or by carbamoyl, dialkylcarbamoyl, sulphamoyl, dialkylsulphamoyl, heteroaryl, aryl, aryloxy, arylthio, arylsulphonyl, aralkoxy, aralkylthio or aralkylsulphonyl, where the heteroaryl and aryl radicals can be monosubstituted, disubstituted or trisubstituted by halogen, cyano, trifluoromethyl, trifluoromethoxy, alkyl, alkoxy, alkylthio or alkylsulphonyl, each of which is identical or different,
or
  denotes heteroaryl which can be monosubstituted, disubstituted or trisubstituted by halogen, alkyl, alkoxy, alkylthio, alkylsulphonyl, aryl, aryloxy, arylthio, arylsulphonyl, trifluoromethyl, trifluoromethoxy, trifluoromethylthio or alkoxycarbonyl, or by a group of the formula —$NR^4R^5$, each of which is identical or different,
wherein
  $R^4$ and $R^5$ have the abovementioned meaning,
or
  denotes aryl which can be monosubstituted to pentasubstituted by alkyl, alkoxy, alkylthio, alkylsulphonyl, aryl, aryloxy, arylthio, arylsulphonyl, aralkyl, aralkoxy, aralkylthio, aralkylsulphonyl, halogen, cyano, nitro, trifluoromethyl, trifluoromethoxy, trifluoromethylthio, alkoxycarbonyl, sulphamoyl, dialkylsulphamoyl, carbamoyl or dialkylcarbamoyl, or by a group of the formula —$NR^4R^5$, each of which is identical or different,
wherein
  $R^4$ and $R^5$ have the abovementioned meaning,
X denotes a group of the formula —$CH_2$—$CH_2$— or —CH=CH—,
and
A denotes a group of the formula

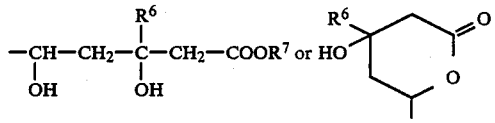

wherein
$R^6$ stands for hydrogen or alkyl,
and
$R^7$
  denotes hydrogen or
  stands for an alkyl, aryl or an aralkyl radical or for a cation,
have now been found.

Surprisingly, the disubstituted pyrroles according to the invention show a superior inhibitory action oN HMG-CoA reductase (3-hydroxy-3-methyl-glutaryl coenzyme A reductase).

Cycloalkyl in general stands for a saturated cyclic hydrocarbon radical having 3 to 8 carbon atoms. The cyclopropyl, cyclopentyl and cyclohexyl ring is preferred. Examples which may be mentioned are cyclopropyl, cyclopentyl, cyclohexyl, cycloheptyl and cyclooctyl.

Alkyl in general stands for a straight-chain or branched saturated hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general stands for a straight-chain or branched hydrocarbon radical having 1 to 12 carbon atoms which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

Alkylsulphonyl in general stands for a straight-chain or branched hydrocarbon radical having 1 to 12 carbon atoms which is bonded via an $SO_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl or isohexylsulphonyl.

Sulphamoyl (aminosulphonyl) stands for the group —$SO_2$—$NH_2$.

Aryl in general stands for an aromatic radical having 6 to about 12 carbon atoms. Preferred aryl radicals are phenyl, naphthyl and biphenyl, in particular phenyl.

Aryloxy in general stands for an aromatic radical having 6 to about 12 carbon atoms which is bonded via an oxygen atom. Preferred aryloxy radicals are phenoxy or naphthyloxy, in particular phenoxy.

Arylthio in general stands for an aromatic radical having 6 to about 12 carbon atoms which is bonded via a sulphur atom. Preferred arylthio radicals are phenylthio or naphthylthio, in particular phenylthio.

Arylsulphonyl in general stands for an aromatic radical having 6 to about 12 carbon atoms which is bonded via an $SO_2$ group. Examples which may be mentioned are: phenylsulphonyl, naphthylsulphonyl and biphenylsulphonyl, in particular phenylsulphonyl.

Aralkyl in general stands for an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl, in particular benzyl.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety and 6 to 12 carbon atoms in the aromatic moiety are preferred. Examples which may be mentioned are the following aralkoxy radicals: benzyloxy, naphthylmethoxy, phenethoxy and phenylpropoxy, in particular benzyloxy.

Aralkylthio in general stands for an aralkyl radical having 7 to about 14 carbon atoms, the alkyl chain being bonded via a sulphur atom. Aralkylthio radicals having 1 to 6 carbon atoms in the aliphatic moiety and 6 to 12 carbon atoms in the aromatic moiety are preferred. Examples which may be mentioned are the following aralkylthio radicals: benzylthio, naphthylmethylthio, phenethylthio and phenylpropylthio, in particular benzylthio.

Aralkylsulphonyl in general stands for an aralkyl radical having 7 to about 14 carbon atoms, the alkyl radical being bonded via an $SO_2$ link. Aralkylsulphonyl radicals having 1 to 6 carbon atoms in the aliphatic moiety and 6 to 12 carbon atoms in the aromatic moiety are preferred. Examples which may be mentioned are the following aralkylsulphonyl radicals: benzylsulphonyl, naphthylmethylsulphonyl, phenethylsulphonyl and phenylpropylsulphonyl, in particular benzylsulphonyl.

Alkoxycarbonyl can be represented, for example, by the formula

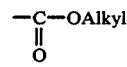

In this connection, alkyl stands for a straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutyoxycarbonyl.

Acyl in general stands for phenyl or straight-chain or branched lower alkyl having 1 to about 6 carbon atoms which are bonded via a carbonyl group. Phenyl and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl, in particular benzoyl and acetyl.

Halogen in general stands for fluorine, chlorine, bromine or iodine, preferably for fluorine, chlorine or bromine. Particularly preferably, halogen stands for fluorine or chlorine.

Heteroaryl in general stands for a 5- to 6-membered aromatic ring which can contain oxygen, sulphur and/or nitrogen as hetero atoms and onto which can be fused further aromatic rings. 5- and 6-membered aromatic rings which contain one oxygen, one sulphur and/or up to 2 nitrogen atoms and which are optionally fused to benzene are preferred. Heteroaryl radicals which may be mentioned as particularly preferred are: thienyl, furyl, pyrolyl, pyrazolyl, pyridyl, pyrimidyl, pyrazinyl, pyridazinyl, quinolyl, isoquinolyl, quinazolyl, quinoxalyl, phthalazinyl, cinnolyl, thiazolyl, benzothiazolyl, isothiazolyl, oxazolyl, benzoxazolyl, isoxazolyl, imidazolyl, benzimidazolyl, pyrazolyl, indolyl and isoindolyl.

If $R^7$ stands for an alkyl, aryl or aralkyl radical, it forms an ester group. Physiologically tolerable esters which were easily hydrolyzed in vivo to a free carboxyl group and a corresponding physiologically tolerable alcohol were preferred. These include, for example, alkyl esters ($C_1$ to $C_4$) and aralkyl esters ($C_7$ to $C_{10}$), preferably lower alkyl esters ($C_1$ to $C_4$) and benzyl esters. The following ester radicals may be mentioned as particularly preferred: methyl esters, ethyl esters, propyl esters and benzyl esters.

$R^7$ can also stand for a cation ($M^{n+}$, where n denotes the valency), preferably a physiologically tolerable metal cation or ammonium cation. Particularly preferred in this connection are alkali metal cations or alkaline earth metal cations such as, for example, sodium, potassium, magnesium or calcium cations, and aluminum ammonium cations, and non-toxic substituted ammonium cations from amines such as dilower alkylamines ($C_1$ to about $C_6$), trilower alkylamines ($C_1$ to about $C_6$), dibenzylamine, N,N'-dibenzylethylenediamine, N-benzyl-β-phenylethylamine, N-methylmorpholine or N-ethylmorpholine, dihydroabietylamine, N,N'-dihydroabietylethylenediamine, N-lower alkylpiperidine and other amines which can be used for the formation of salts.

In the context of the present invention, the disubstituted pyrroles can be represented by the general formulae (Ia–f)

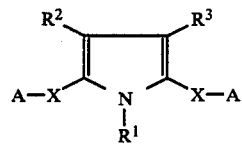
(Ia)

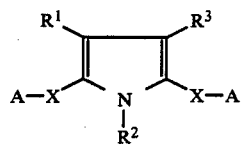
(Ib)

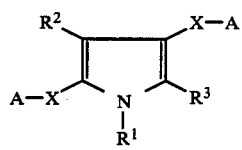
(Ic)

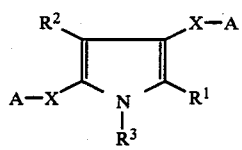
(Id)

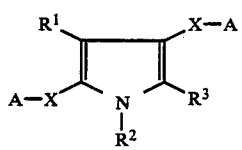
(Ie)

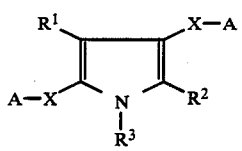
(If)

in which $R^1$, $R^2$, $R^3$, X and A have the abovementioned meaning.

Preferred compounds of the general formulae (I) are those in which $R^1$ denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by fluorine, chlorine, bromine, lower alkyl, lower alkoxy, phenyl, phenoxy, trifluoromethyl, trifluoromethoxy or lower alkoxycarbonyl, each of which is identical or different, or denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula $-NR^4R^5$, each of which is identical or different, where $R^4$ and $R^5$ are identical or different and denote lower alkyl, phenyl, benzyl, acetyl, benzoyl, phenylsulphonyl or lower alkylsulphonyl, $R^2$ denotes cyclopropyl, cyclopentyl or cyclohexyl, or denotes lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl, or by a group of the formula $-NR^4R^5$, wherein $R^4$ and $R^5$ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by fluorine, chlorine, bromine, lower alkyl, lower alkoxy, trifluoromethyl or trifluoromethoxy, each of which is identical or different, $R^3$ denotes hydrogen, or denotes cyclopropyl, cyclopentyl or cyclohexyl, or denotes lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl or by a group of the formula $-NR^4R^5$, wherein $R^4$ and $R^5$ have the abovementioned meaning, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heteroaryl and aryl radicals mentioned can be monosubstituted or disubstituted by fluorine, chlorine, bromine, lower alkyl, lower alkoxy, trifluoromethyl or trifluoromethoxy, each of which is identical or different, denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, quinolinyl, benzothiazolyl, benzoxazolyl or benzimidazolyl, each of which can be monosubstituted or disubstituted by fluorine, chlorine, bromine, lower alkyl, lower alkoxy, phenyl, phenoxy, trifluoromethyl, trifluoromethoxy or lower alkoxycarbonyl, each of which is identical or different, or denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula $-NR^4R^5$, each of which is identical or different, where
$R^4$ and $R^5$ have the abovementioned meaning,
X denotes a group of the formula $-CH=CH-$
and
A denotes a group of the formula

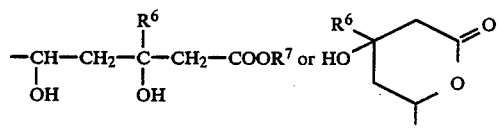

wherein
$R^6$
denotes hydrogen or lower alkyl,
and
$R^7$
denotes a $C_1$ to $C_6$ alkyl radical, a $C_6$ to $C_{12}$ aryl radical or a $C_7$ to $C_{10}$ aralkyl radical, or
denotes a physiologically tolerable cation.

Particularly preferred compounds of the general formula I are those in which
$R^1$
denotes pyridyl, pyrimidyl, quinolyl or isoquinolyl, each of which can be substituted by fluorine, chlorine, methyl, methoxy or trifluoromethyl, or
denotes phenyl which can be monosubstituted, disubstituted or trisubstituted by methyl, ethyl, propyl, isopropyl, butyl, isobutyl, tert.butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tert.butoxycarbonyl, each of which is identical or different,
$R^2$ denotes cyclopropyl, cyclopentyl or cyclohexyl, or denotes methyl, ethyl, propyl, isopropyl, butyl, sec.-butyl or tert.butyl, each of which can be substituted by fluorine, chlorine, bromine, cyano, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl, $R^3$
denotes hydrogen, cyclopropyl, cyclopentyl or cyclohexyl, or denotes methyl, ethyl, propyl, isopropyl, butyl, isobutyl, tert.butyl, pentyl, isopentyl, hexyl or isohexyl, each of which can be substituted by fluorine, chlorine, bromine, cyano, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group $-NR^4R^5$, where
$R^4$ and $R^5$ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl, or by pyridyl, pyrimidyl, pyrazinyl, pyridazinyl, quinolyl, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.-butoxy, trifluoromethyl or trifluoromethoxy, or denotes thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzothiazolyl, where the radicals mentioned can be substituted by fluorine, chlorine, methyl, ethyl, propyl, isopropyl, butyl, isobutyl, tert.butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or denotes phenyl which can be monosubstituted, disubstituted or trisubstituted by methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl or tert.butoxycarbonyl, or by a group —$NR^4R^5$, each of which is identical or different, where $R^4$ and $R^5$ have the abovementioned meaning, X denotes a group of the formula —CH=CH— and

A denotes a group of the formula

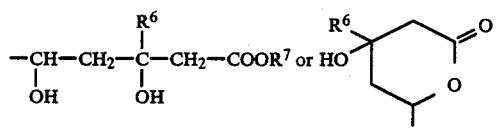

wherein $R^6$ denotes hydrogen, methyl, ethyl, propyl, isopropyl, butyl, isobutyl or tert.butyl and $R^7$ denotes hydrogen, methyl, ethyl, propyl, isopropyl, butyl, isobutyl, tert.butyl or benzyl, or denotes a sodium, potassium, calcium or magnesium or ammonium ion.

Very particularly preferred compounds of the general formulae I are those in which $R^1$ denotes phenyl which can be monosubstituted or disubstituted by methyl, phenoxy, fluorine or trifluoromethyl, each of which is identical or different, $R^2$ denotes isopropyl, cyclopropyl or tert.butyl, $R^3$ denotes cyclopropyl, isopropyl, tert.-butyl or phenyl, each of which can be monosubstituted or disubstituted by fluorine, methyl, phenoxy or trifluoromethyl, each of which is identical or different, X denotes a group of the formula

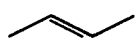 (E configuration)

and

A denotes a group of the formula

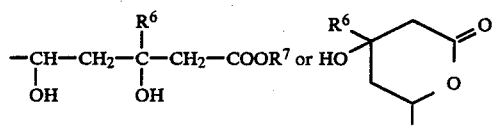

wherein $R^6$ denotes hydrogen and $R^7$ denotes hydrogen, methyl or ethyl, or denotes a sodium or potassium cation.

The disubstituted pyrroles of the general formula (I) according to the invention have several asymmetric carbon atoms and can therefore exist in various stereochemical forms. The invention relates to both the individual isomers and their mixtures.

The isomers of the general formula (I) which are substituted in the 2,5 and 3,5-positions with the radical X-A are particularly preferred.

Depending on the meaning of the groups X or the radicals A, different stereoisomers result which are illustrated in more detail in the following:

(a) if the group —X— stands for a group of the formula —CH=CH—, then the compounds according to the invention can exist in two stereoisomeric forms which can have the E configuration (II) or the Z configuration (III) on the double bond:

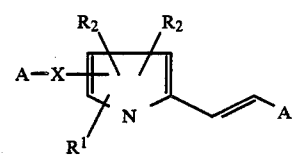 (II) E form

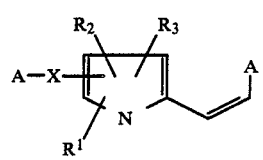 (III) Z form

Those compounds of the general formula (I) which have the E configuration (II) are preferred.

$R^1$, $R^2$, $R^3$, X and A have the abovementioned meaning.

(b) If the radical —A— stands for a group of the formula

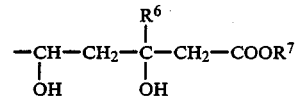

then the compounds of the general formula (I) have at least two asymmetric carbon atoms, namely the two carbon atoms to which the hydroxyl groups are bonded. Depending on the relative position of these hydroxyl groups to one another, the compounds according to the invention can be present in the erythro configuration (IV) or in the threo configuration (V).

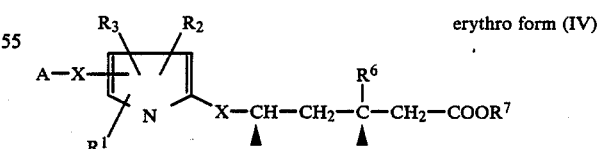 erythro form (IV)

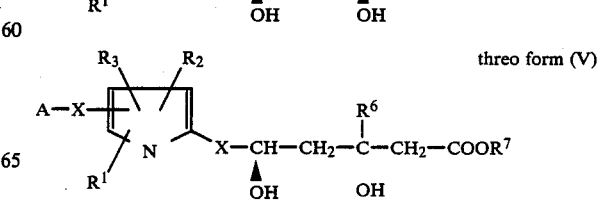 threo form (V)

Two enantiomers again exist in each case both of the compounds of the erythro and the threo configuration, namely the 3R,5S-isomer or the 3S,5R-isomer (erythro form) and the 3R,5R-isomer and the 3S,5S-isomer (threo form).

The isomers having the erythro configuration are preferred in this connection, particularly preferably the 3R,5S-isomer and the 3R,5S-3S,5R-racemate.

(c) If the radical —A stands for a group of the formula

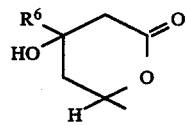

then the disubstituted pyrroles possess at least two asymmetric carbon atoms, namely the carbon atom to which the hydroxyl group is bonded, and the carbon atoms to which the radical

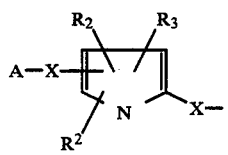

is bonded. Depending on the position of the hydroxyl group to the free valency on the lactone ring, the disubstituted pyrroles can be present as cis-lactones (VI) or as trans-lactones (VII).

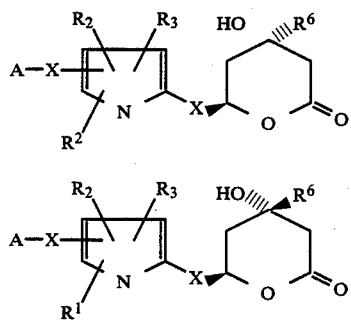

cis-lactone(IV)

trans-lactone(VII)

Two isomers again exist in each case of both the cis-lactone and the trans-lactone, namely the 4R,6R-isomer or the 4S,6S-isomer (cis-lactone), and the 4R,6S-isomer or 4S,6R-isomer (trans-lactone). Preferred isomers are the trans-lactones. The 4R,6S-isomer (trans) and the 4R,6S-4S,6R-racemate are preferred in this connection.

For example, the following isomeric forms of the substituted pyrroles may be mentioned:

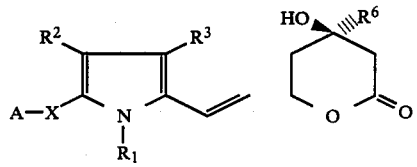

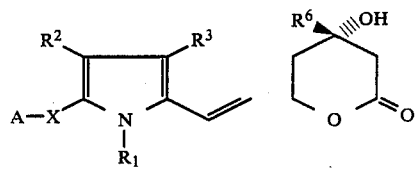

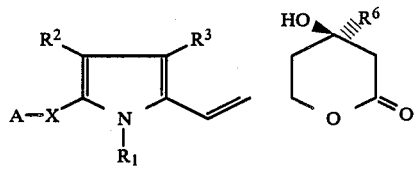

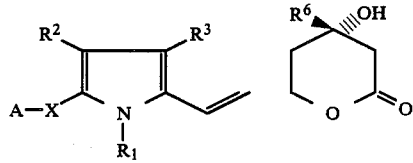

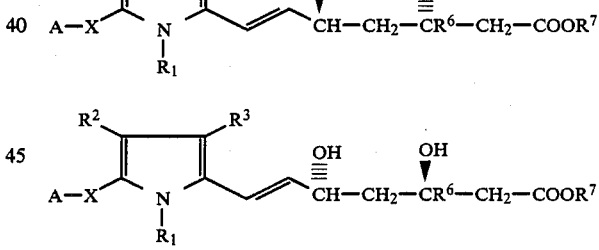

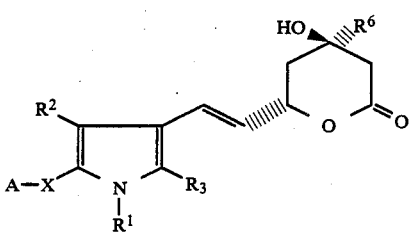

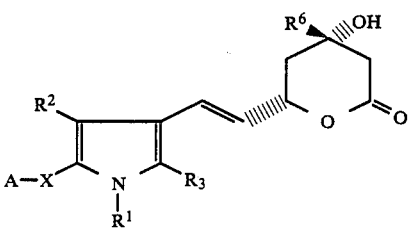

-continued

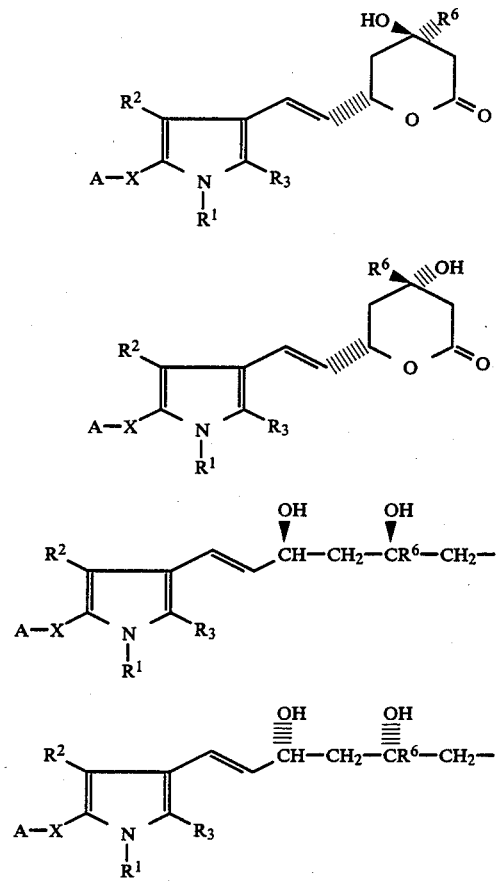

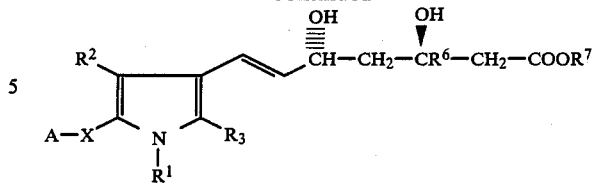

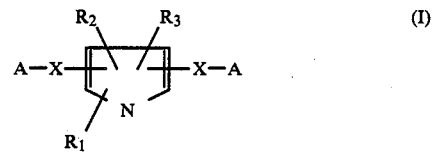

Moreover, further possibilities for the formation of isomers result since the disubstituted pyrroles according to the invention are substituted by two groups of the formula —X—A. The abovementioned also applies to the second group —X—A in the molecule. The invention likewise relates to all stereoisomers which result by means of the second group of the formula —X—A, in particular in connection with the first group —X—A.

Moreover, further possibilities result since the disubstituted pyrroles according to the invention are characterized by the variation in relation to the position of the radicals $R_1$, $R_2$ and $R_3$.

In addition, a process for the preparation of the disubstituted pyrroles of the general formula (I)

$$\text{(I)}$$

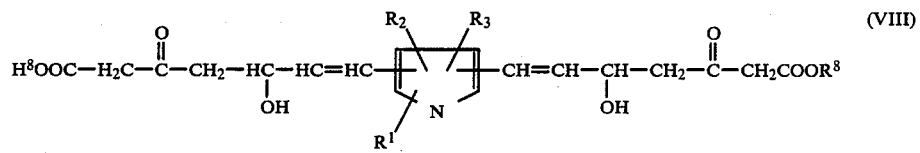

in which $R^1$, $R^2$, $R^3$ and A and X have the abovementioned meaning, has been found, which is characterized in that ketones of the general formula (VIII)

(VIII)

in which
$R^1$, $R^2$ and $R^3$ have the abovementioned meaning, and $R^8$ stands for alkyl,
are reduced, in the case of the preparation of the acids, the esters are hydrolyzed, in the case of the preparation of the lactones, the carboxylic acids are cyclized, in the case of the preparation of the salts, either the esters or the lactones are hydrolyzed, in the case of the preparation of the ethylene compounds (X=—CH$_2$—CH$_2$—), the ethene compounds (X=—CH=CH—) are hydrogenated by customary methods, and, if appropriate, isomers are resolved.

The process according to the invention can be illustrated by the following equation:

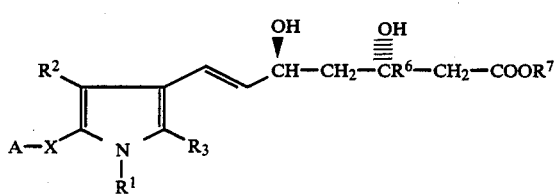

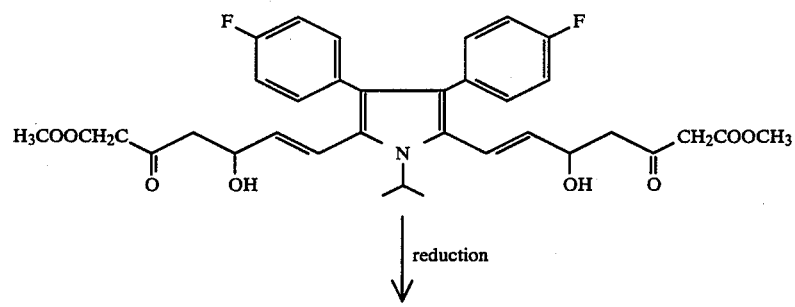
↓ reduction
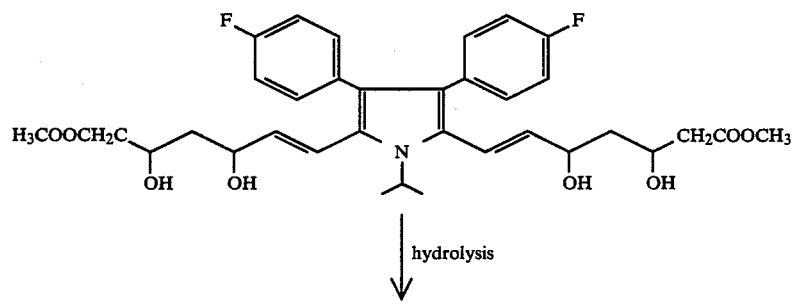
↓ hydrolysis
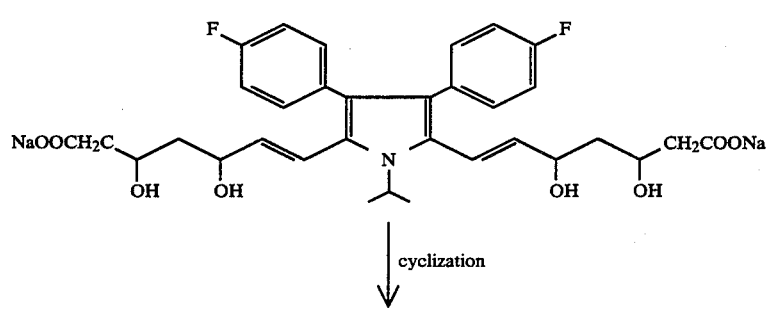
↓ cyclization
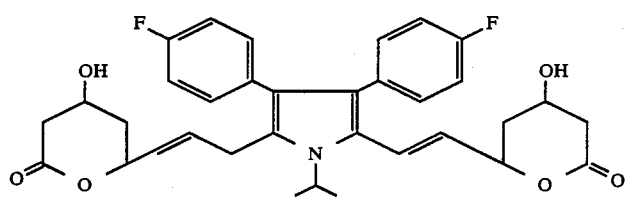
or
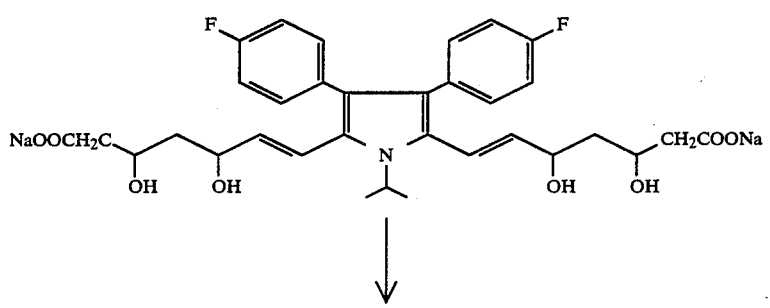
↓

-continued

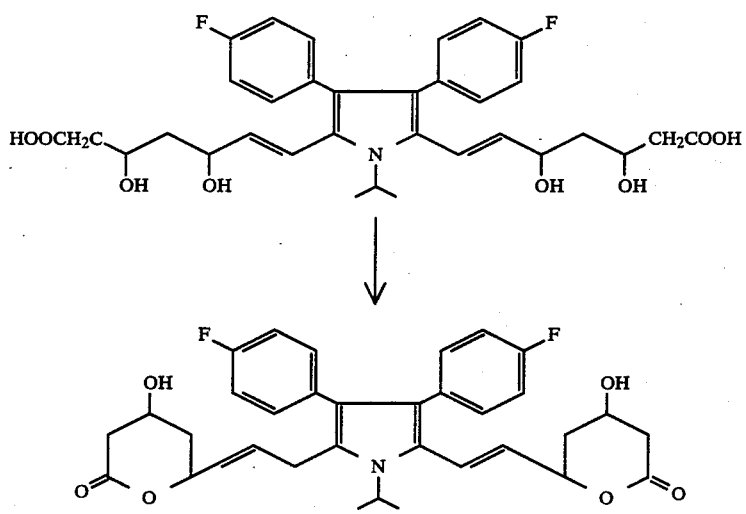

The reduction can be carried out using the customary reducing agents, preferably using those which are suitable for the reduction of ketones to hydroxyl compounds. Reduction using metal hydrides or complex metal hydrides in inert solvents, if desired in the presence of a trialkylborane, is particularly suitable in this connection. Reduction is preferably carried out using complex metal hydrides, such as, for example, lithium borohydride, sodium borohydride, potassium borohydride, zinc borohydride, lithium trialkyl borohydrides, sodium trialkyl borohydrides, sodium cyanoborohydride or lithium aluminum hydride. Reduction is very particularly preferably carried out using sodium borohydride in the presence of triethylborane.

Suitable solvents in this connection are the customary organic solvents, which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is likewise possible to employ mixtures of the solvents mentioned.

Reduction of the ketone group to the hydroxyl group is particularly preferably carried out under conditions in which the other functional groups such as, for example, the alkoxycarbonyl group, are not changed. The use of sodium borohydride as reducing agent, in the presence of triethylborane in inert solvents such as, preferably, ethers, is particularly suitable for this.

The reduction is in general carried out in a temperature range from $-90°$ C. to $+30°$ C., preferably from $-80°$ C. to $0°$ C.

The process according to the invention is in general carried out at atmospheric pressure. However, it is also possible to carry out the process at underpressure or at overpressure (for example in a range from 0.5 to 5 bar).

In general, the reducing agent is employed in an amount from 1 to 2 moles, preferably from 1 to 1.5 moles, based on 1 mole of the keto compound.

Under the abovementioned reaction conditions, the carbonyl group is in general reduced to the hydroxyl group without reduction of the double bond to a single bond taking place.

To prepare compounds of the general formula (I) in which X stands for an ethylene grouping, the reduction of the ketones (VIII) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ig)

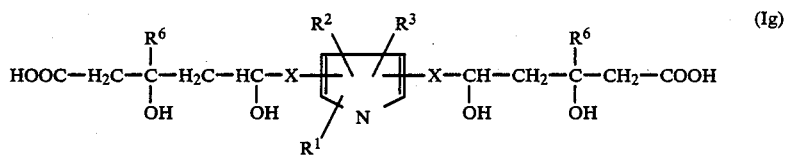

in which $R^1$, $R^2$, $R^3$, $R^6$ and X have the abovementioned meaning.

The carboxylic acid esters in the context of the general formula (I) correspond to the formula (Ih)

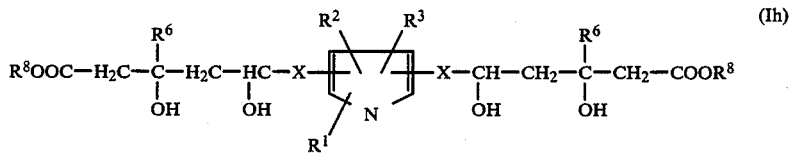

(Ih)

in which

R$^1$, R$^2$, R$^3$, R$^6$ and X have the abovementioned meaning, and

R$^8$ stands for alkyl.

The salts of the compound according to the invention in the context of the general formula (I) correspond to the formula (Ii)

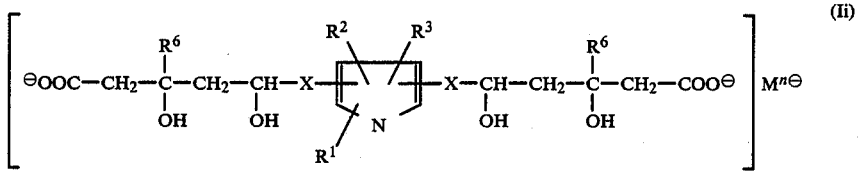

(Ii)

in which

R$^1$, R$^2$, R$^3$, R$^6$ and X have the abovementioned meaning, and

M$^{n+}$ stands for an n-valent cation.

The lactones in the context of the general formula (I) correspond to the formula (Ij)

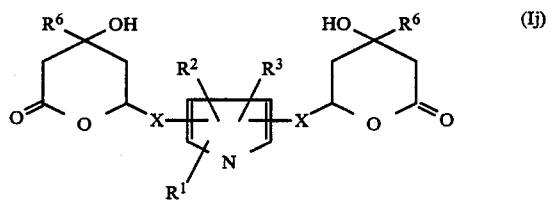

(Ij)

in which R$^1$, R$^2$, R$^3$, R$^6$ and X have the abovementioned meaning.

To prepare the carboxylic acids of the general formula (Ig) according to the invention, the carboxylic acid esters of the general formula (Ih) or the lactones of the general formula (Ij) are in general hydrolyzed by customary methods. Hydrolysis is in general carried out by treating the esters or the lactones with customary bases in inert solvents, by means of which the salts of the general formula (Ii) in general initially result, which can subsequently be converted into the free acids of the general formula (Ig) in a second step by treating with acid.

Suitable base for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate, or sodium hydrogen carbonate, or alkali metal alkoxides such as sodium ethoxide, sodium methoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is likewise possible to employ mixtures of the solvents mentioned.

The hydrolysis is in general carried out in a temperature range from 0° C. to +100° C., preferably from +20° C. to +80° C.

In general, the hydrolysis is carried out at atmospheric pressure. However, it is also possible to work at underpressure or at overpressure (for example from 0.5 to 5 bar).

When carrying out the hydrolysis, the base is in general employed in an amount from 1 to 3 moles, preferably 1 to 1.5 moles, relative to 1 mole of the ester or the lactone. Molar amounts of reactants are particularly preferably used.

When carrying out the reaction, the salts of the compounds (Ii) according to the invention result in the first step as intermediates which can be isolated.

The acids (Ig) according to the invention are obtained by treating the salts (Ii) with customary inorganic acids. These preferably include mineral acids such as, for example, hydrochloric acid, hydrobromic acid, sulphuric acid or phosphoric acid. It has also proved advantageous in this connection in the preparation of the carboxylic acids (Ig) to acidify the basic reaction mixture from the hydrolysis in a second step without isolation of the salts. The acids can then be isolated in a customary manner.

To prepare the lactones of the formula (Ij) according to the invention, the carboxylic acids (Ig) according to the invention are in general cyclized by customary methods, for example by heating the corresponding acid in inert organic solvents, if desired in the presence of molecular sieves.

Suitable solvents in this connection are hydrocarbons such as benzene, toluene, xylene, mineral oil fractions, or tetralin or diglyme or triglyme. Benzene, toluene or xylene are preferably employed. It is likewise possible to employ mixtures of the solvents mentioned. Hydrocarbons, in particular toluene, are particularly preferably used in the presence of molecular sieves.

The cyclization is in general carried out in a temperature range from −40° C. to +200° C., preferably from −25° C. to +50° C.

The cyclization is in general carried out at atmospheric pressure, but it is also possible to carry out the process at underpressure or at overpressure (for example in a range from 0.5 to 5 bar).

Moreover, the cyclization is also carried out in inert organic solvents, with the aid of cyclizing or dehydrating agents. Carbodiimides are preferably used as dehydrating agents in this connection. N,N'-Dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride are preferably employed as carbodiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene or mineral oil fractions are particularly preferred. Chlorinated hydrocarbons such as, for example, methylene, chloride, chloroform or carbon tetrachloride are particularly preferably employed.

The reaction is in general carried out in a temperature range from 0° C. to +80° C., preferably from +10° C. to +50° C.

When carrying out the cyclization, it has proved advantageous to employ the cyclization method with the aid of carbodiimides as dehydrating agents.

The resolution of the isomers into the stereoisomerically homogeneous constituents is in general carried out by customary methods such as are described, for example, by E. L. Eliel, Stereochemistry of Carbon Compounds, McGraw Hill, 1962. Resolution of the isomers from the racemic lactone step is preferred in this connection. The racemic mixture of the trans-lactones (VII) is particularly preferably converted in this connection into the diastereomeric dihydroxyamides (Ik)

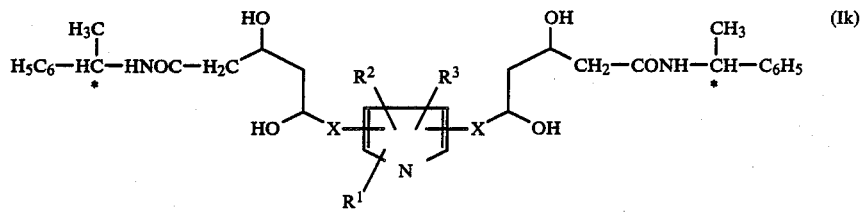

by treating either with D-(+)- or L-(−)-α-methylbenzylamine by customary methods, which can subsequently be resolved into the individual diastereomers by chromatography or crystallization as is customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, yields the corresponding pure enantiomeric dihydroxy acids (Ig) which can be converted into the pure enantiomeric lactones by cyclization as described above. In general, it applies to the preparation of the compounds of the general formula (I) according to the invention in pure enantiomeric form that the configuration of the final products after the methods described above is dependent on the configuration of the starting materials.

The resolution of isomers is illustrated by way of example in the following scheme:

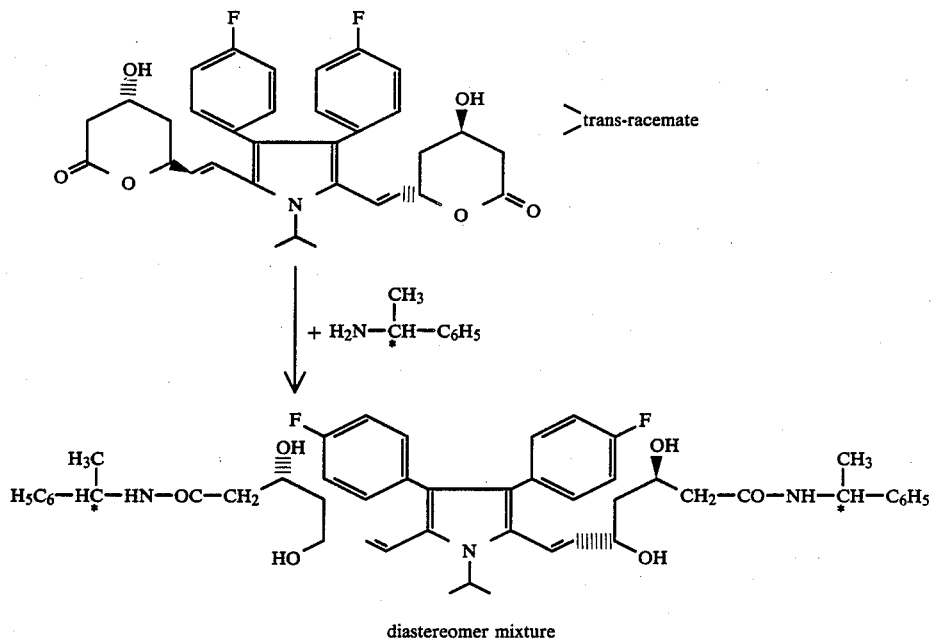

1. resolution of diastereomers
2. hydrolysis 3. lactonization

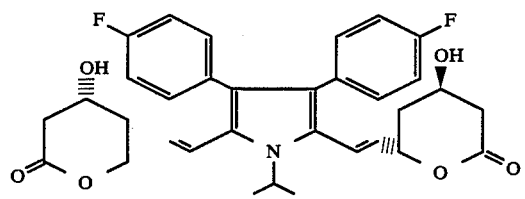

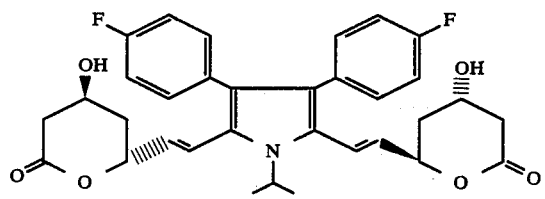

The ketones (VIII) employed as starting materials are new.

A process for the preparation of the ketones of the general formula (VIII) according to the invention

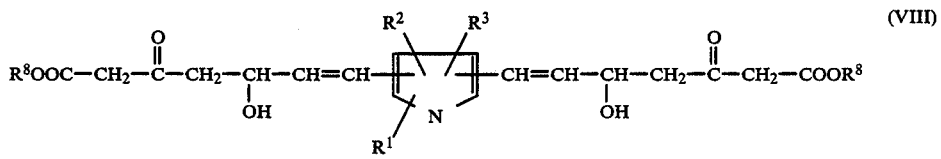

in which $R^1$, $R^2$, $R^3$ and $R^8$ have the abovementioned meaning, has been found which is cahracterized in that aldehydes of the general formula (IX)

(IX)

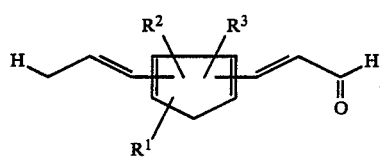

in which $R^1$, $R^2$ and $R^3$ have the abovementioned meaning, are reacted in inert solvents with acetoacetates of the general formula (X)

in which $R^8$ has the abovementioned meaning, in the presence of bases.

The process according to the invention can be illustrated, for example, by the following equation:

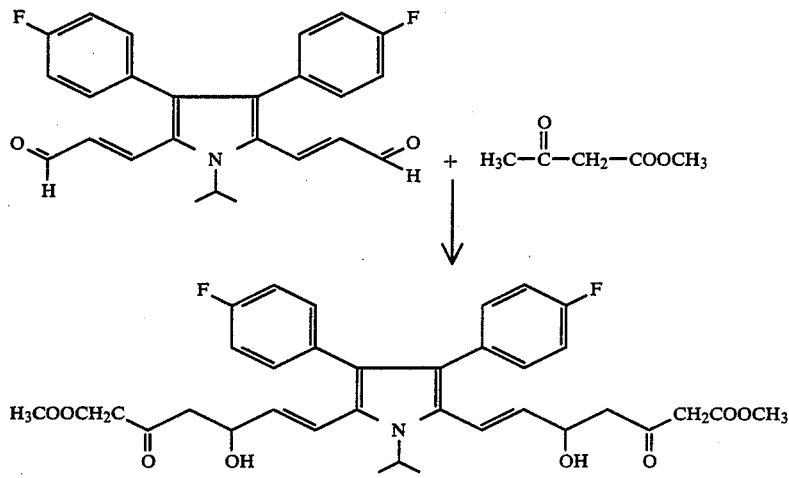

Suitable bases in this connection are the customary strong basic compounds. The reaction is also carried out in the presence of zinc salts. These preferably include organolithium compounds, such as, for example, n-butyllithium, sec.butyllithium, tert.butyllithium or phenyllithium or amides such as, for example, lithium diisopropylamide, sodium amide or potassium amide, or lithium hexamethyldisilylamide, or alkali metal hydrides such as sodium hydride or potassium hydride. It is likewise possible to employ mixtures of the bases mentioned. n-Butyllithium, sodium hydride or a mixture thereof in the presence of zinc bromide is particularly preferred.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is likewise possible to employ mixtures of the solvents mentioned. Ethers such as diethyl ether or tetrahydrofuran are particularly preferably used.

The reaction is in general carried out in a temperature range from −80° C. to +50° C., preferably from −20° C. to +30° C.

The process is in general carried out at atmospheric pressure, but it is also possible to carry out the process at underpressure or at overpressure, for example in a range from 0.5 to 5 bar.

When carrying out the process, the acetoacetate is in general employed in an amount from 1 to 2, preferably from 1 to 1.5, moles relative to 1 mole of the aldehyde.

The acetoacetates of the formula (X) employed as starting materials are known or can be prepared by known methods [Beilstein's Handbuch der organischen Chemie (Beilstein's Handbook of Organic Chemistry) III, 632; 438].

Acetoacetates which may be mentioned, for example, for the process according to the invention are: methyl acetoacetate, ethyl acetoacetate, propyl acetoacetate and isopropyl acetoacetate.

The aldehydes of the general formula (IX) employed as starting materials are new.

A process for the preparation of the aldehydes of the general formula (IX)

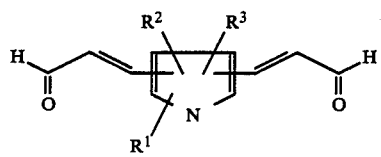

in which $R^1$, $R^2$ and $R^3$ have the abovementioned meaning, has additionally been found, which is characterized in that pyrroles of the general formula (XI)

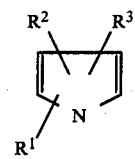

(XI)

in which $R^1$, $R^2$ and $R^3$ have the abovementioned meaning, are reacted in inert solvents in the presence of auxiliaries with N,N-dialkylaminoacrolein of the formula (XII)

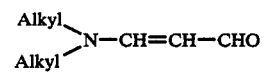

(XII)

where alkyl stands for a straight-chain or branched carbon radical having 1 to 6 carbon atoms.

The process according to the invention can be illustrated, for example, by the following equation:

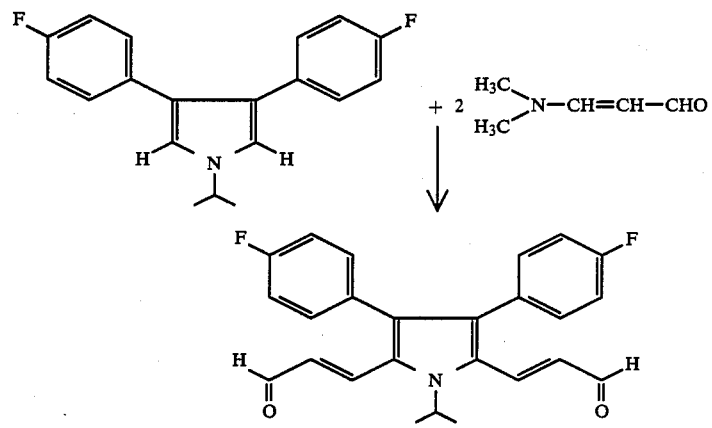

Suitable solvents in this connection are the customary organic solvents which are stable under the reaction conditions. These preferably include hydrocarbons such as benzene, toluene, xylene, hexane, mineral oil fractions, chlorobenzene or o-dichlorobenzene, or ethers such as diethyl ether, dioxane or tetrahydrofuran, or chlorinated hydrocarbons such as methylene chloride, chloroform or carbon tetrachloride, or acetonitrile. It is likewise possible to employ mixtures of the solvents mentioned. Anhydrous acetonitrile or chloroform is particularly preferably used.

Acid chlorides are in general used as auxiliaries. Phosphorus oxychloride or phosgene is preferably employed, particularly preferably phosphorus oxychloride.

The reaction is carried out in a temperature range from −20° C. to +150° C., preferably from 0° C. to 100° C.

The process is in general carried out at atmospheric pressure. However, it is also possible to carry out the process at underpressure or at overpressure (for example in a range from 0.5 to 5 bar).

When carrying out the process, the dimethylaminoacrolein is in general employed in an amount from 1 to 6, preferably from 1.2 to 3, moles relative to 1 mole of the pyrrole.

The pyrroles of the general formula (XI) employed as starting materials are known or can be prepared by known methods [A. Glossauer "Die Chemie der Pyrrole" ("The Chemistry of Pyrroles"), Springer Verlag Berlin, 1974].

The disubstituted pyrroles according to the invention can be used in medicaments for therapeutic treatment in humans and in animals. Preferably, they can be used as inhibitors of 3-hydroxy-3-methylglutaryl coenzyme A (HMG-CoA) reductase and inhibitors of cholesterol biosynthesis. They can therefore be employed for the treatment of hyperlipoproteinaemia, lipoproteinaemia or arteriosclerosis. The active compounds according to the invention additionally cause a lowering of the cholesterol content in the blood.

The new active compounds can be converted in a known manner into the customary formulations, such as tablets, coated tablets, pills, granules, aerosols, syrups emulsions, suspensions and solutions, using inert, non-toxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient to achieve the dosage range indicated.

The formulations are prepared, for example, by extending the active compound using solvents and/or excipients, optionally using emulsifiers and/or dispersants, where, for example, in the case of the use of water as a diluent, organic solvents can be used, if desired, as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, argillaceous earths, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium lauryl sulphate).

Administration is carried out in a customary manner, preferably orally, parenterally, perlingually or intravenously. In the case of oral administration, tablets can, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tabletting. In the case of aqueous suspensions, various flavor improvers or colorants can be added to the active compounds in addition to the above-mentioned auxiliaries.

In the case of parenteral administration, solutions of the active compounds can be employed using suitable liquid excipients.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this, it may sometimes be necessary to deviate from the amounts mentioned, depending on the body weight or the type of application route, on individual behavior towards the medicament, the manner of its formulation and the point in time or interval at which administration takes place. Thus, in some cases it may be sufficient to manage with less than the minimum amount previously mentioned, whereas in other cases the upper limit mentioned must be exceeded. In the case of administration of larger amounts, it may be advisable to divide these into a number of individual doses over the day.

Starting Compounds and Preparation Examples

EXAMPLE 1

1,2-Bis-(4-fluorophenyl)-acrylonitrile

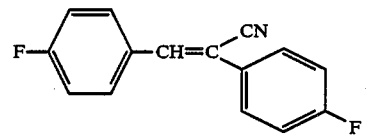

A solution of 2.3 g of sodium in 35 ml of ethanol is added dropwise to a solution of 137.7 g (1.11 mol) of 4-fluorobenzaldehyde and 150 g (1.11 mol) of 4-fluorobenzyl cyanide in 900 ml of ethanol at 50° C. During the course of this a voluminous colorless precipitate deposits which is filtered off with suction after stirring for 1 hours without heating. The precipitate is washed with water and dried over phosphorus pentoxide in a high vacuum.

Yield: 258 g (96% of theory).
Melting point: 164° C.,

EXAMPLE 2

2-Ethoxycarbonyl-3,5-bis-(4-fluorophenyl)-pyrrole

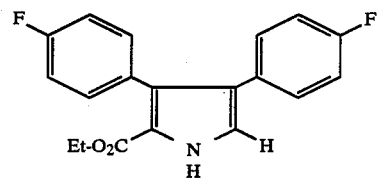

A warm solution of 18 g (0.16 mol) of ethyl isocyanoacetate and 29.4 g (0.12 mol) of the compound from Example 1 in 15 ml of dimethyl sulphoxide and 125 ml of tetrahydrofuran is added dropwise at $-15°$ C. to a suspension of 5.1 g (0.17 mol) of 80% strength sodium hydride in 125 ml of anhydrous tetrahydrofuran, and the mixture is stirred for a further hour at $-15°$ C. and finally for 30 minutes at room temperature. Water is now cautiously added dropwise, the aqueous phase is separated off and extracted three times using ethyl acetate, and the combined organic phases are washed with saturated sodium chloride solution. After drying over sodium sulphate, they are concentrated to give a brown oil (48 g) which is filtered over 200 g of silica gel using toluene. 16.2 g (41% of theory) of almost colorless crystals of melting point 138° C. crystallize from ether.

EXAMPLE 3

2-Ethoxycarbonyl-3,4-bis(4-fluorophenyl)-1-isopropyl-pyrrole

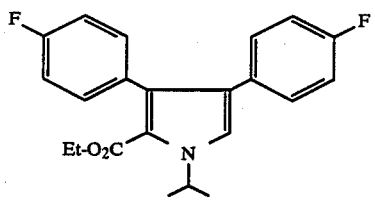

10 g (30.6 mmol) of the compound from Example 2 in 50 ml of tetrahydrofuran, followed by 15.6 g (91.8 mmol) of isopropyl iodide are added dropwise at 0° C. to 5.14 g (45.8 mmol) of potassium tertiary butoxide in 40 ml of anhydrous tetrahydrofuran. The mixture is boiled under reflux for 18 hours and then poured into 300 ml of ice water. After addition of 300 ml of water, the mixture is extracted three times using 150 ml of ethyl acetate each time, and the organic phase is washed with saturated sodium chloride solution, dried over sodium sulphate and concentrated (13 g of brown oil). After filtering over 100 g of silica gel (230–400 mesh) using petroleum ether/dichloromethane (3:1), 9.2 g (81% of theory) of faintly colored oil are obtained, which solidifies in a refrigerator. Melting point: 49° C.

$^1$H-NMR (CDCl$_3$): δ=0.95 (t, 3H, CH$_2$C$\underline{H}_3$), 1.53 (d, 6H, CH—(C$\underline{H}_3$)$_2$); 4.05 (q, 2H, C$\underline{H}_2$—CH$_3$); 5.43 (sept, 1H, C$\underline{H}$(CH$_3$)$_2$; 6.8–7.2 (m, 9H, 5H+aromatic H).

EXAMPLE 4

3,4-Bis-(4-fluorophenyl)1-isopropyl-pyrrole-2-carboxylic acid

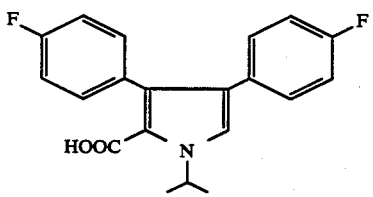

6.8 g (18.4 mol) of the compound from Example 3 are heated to reflux for 18 hours in 30 ml of ethanol and 3.4 ml of 6N sodium hydroxide solution. The mixture is then acidified using 1N hydrochloric acid and the deposited precipitate is filtered off with suction. The precipitate is dissolved again in ethyl acetate, extracted using 1N hydrochloric acid and saturated sodium chloride solution, dried over sodium sulphate and concentrated to dryness. Recrystallization from ether/petroleum ether yields 4.35 g (69% of theory) of colorless crystals of melting point 212° C.

EXAMPLE 5

3,4-Bis-(4-fluorophenyl)-1-isopropyl-pyrrole

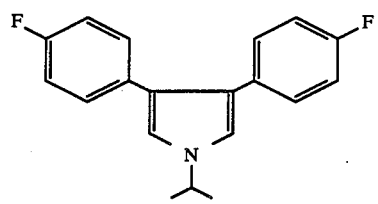

A 4.6 g (13.5 mmol) of the compound from Example 4 are heated to reflux for 30 minutes in 15 ml of acetic acid. The acetic acid is stripped off in vacuo, the residue is dissolved in dichloromethane, and the solution is washed with sodium hydrogen carbonate solution and sodium chloride solution and dried over sodium sulphate. After concentrating, 3.9 g (97% of theory) of colorless crystals of melting point 105° C. remain.

B

A solution of 3.37 g (13.2 mmol) of the compound from Example 11 in 15 ml of tetrahydrofuran is added dropwise with ice cooling to 2.22 g (19.8 mmol) of potassium tertiary butoxide in 15 ml of tetrahydrofuran. (39.6 mmol) of isopropyl iodide are then added dropwise at room temperature and the mixture is heated to reflux for 3 hours.

After addition of 50 ml of water, the mixture is extracted three times using methylene chloride, and the combined organic phases are dried and concentrated to give a yellow oil. Filtration over 50 g of silica gel using petroleum ether/methylene chloride (10:1) gives 2.13 g (54%) of slightly colored crystals of melting point 104° C. (identical by TLC with the sample obtained by process A).

EXAMPLE 6

3,4-Bis-(4-fluorophenyl)-2,5-bis-(2-formyl-ethenyl)-1-isopropyl-pyrrole

A solution of 4.3 g (39.1 mmol) of 90% strength dimethylaminoacrolein in 10 ml of acetonitrile is added dropwise at −5° C. to 3.82 ml (41.9 mmol) of phosphorus oxychloride in 20 ml of anhydrous acetonitrile and 2.1 g (7.1 mmol) of the compound from Example 5 are then added in portions. The mixture is heated to reflux for 18 hours, then added to a cold emulsion of 200 ml of toluene and 200 ml of water, in which 13 g of sodium hydroxide are dissolved, and stirred vigorously at room temperature for 1.5 hours. The mixture is filtered with suction over silica gel, and the organic phase is dried over sodium sulphate and concentrated to give a black oil (3.2 g). Column chromatography on 60 g of silica gel (230–400 mesh) using 300 ml each of toluene, toluene-/ethyl acetate (10:1), (5:1) and (3:1) gives two fractions: 0.88 g (36%) of 3,4-bis-(4-fluorophenyl)-2-(2-formylethenyl)-1-isopropyl-pyrrole elutes first as weakly colored crystals of melting point 153° C., then the product, 1.4 g of yellow foam, which recrystallizes from ether/petroleum ether gives 1.12 g (39%) of orange-colored crystals of melting point 207° C.

EXAMPLE 7

3,4-Bis-(4-fluorophenyl)-2,5-bis-(3-hydroxy-6-methoxycarbonyl-5-oxo-hex-1-enyl)-1-isopropyl-pyrrole

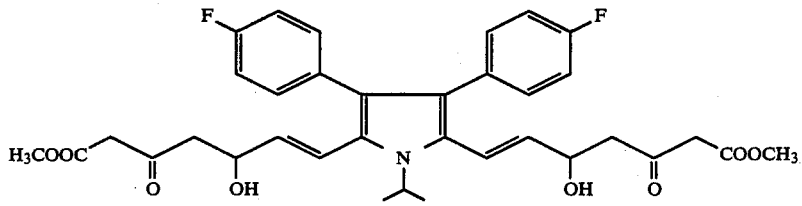

0.35 ml (3.25 mmol) of methyl acetoacetate and then at about 0° C. 2.72 ml (4.43 mmol) of a 15% strength solution of butyllithium in hexane are added slowly under argon to a suspension of 107 mg (3.56 mmol) of 80% strength sodium hydride in 10 ml of anhydrous tetrahydrofuran at −5° C. After stirring for 15 minutes at 0° C., a solution of 0.6 g (1.48 ml) of the compound from Example 6 in 5 ml of tetrahydrofuan is added dropwise and the mixture is stirred for a further 15 minutes at the same temperature. Finally, 0.58 g (9.67 mmol) of acetic acid is cautiously added dropwise and then 50 ml of water, the mixture is extracted three times using ethyl acetate and the organic phase is dried over sodium sulphate and sodium carbonate. After stripping off the solvent, 0.94 g of reddish foam remain of $R_f$ value: 0.2 using toluene/ethyl acetate (1:1). The crude product is processed further.

EXAMPLE 8

3,4-Bis-(4-fluorophenyl)-2,5-bis-(3,5-dihydroxy-6-methoxycarbonyl-hex-1-enyl)-1-isopropyl-pyrrole

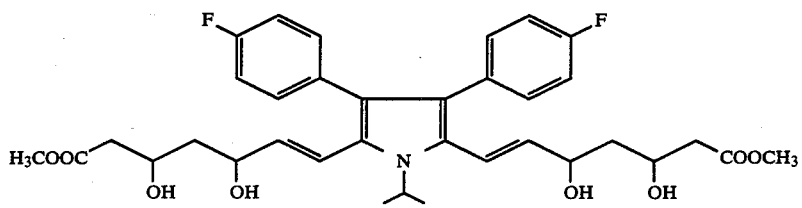

3.56 ml of a 1M solution of triethylborane in tetrahydrofuran are added dropwise at room temperature under argon to a solution of 0.94 g (1.48 mol) of the compound from Example 7 in 10 ml of anhydrous tetrahydrofuran and air is passed through the solution for 5 minutes. After cooling to −78° C., 138 mg (3.64 mol) of sodium borohydride are added, then 1.96 ml of anhydrous methanol are added dropwise slowly so that the temperature remains under −65° C., and the mixture is stirred at −75° C. for 15 minutes and at −30° C. for 15 minutes, before 9.9 ml of 30% strength hydrogen peroxide in 30 ml of water are added dropwise at 0° C. After warming to room temperature, the mixture is extracted three times using 30 ml of ethyl acetate, and the combined organic phases are washed with saturated sodium chloride solution, dried over sodium sulphate and sodium carbonate and concentrated to give a red-brown foam (850 mg). After column chromatography twice on the 30-fold amount of silica gel (230–400 mesh), first with toluene/ethyl acetate (1:1) and ethyl acetate, secondly with dichloromethane/ethyl acetate (1:1) and (1:3), 102 mg (11% of theory) of almost colorless amorphous solid are obtained.

$R_f$=0.3, ethyl acetate.

$^1$H-NMR (CDCl$_3$): δ=1.3–1.6 (m, 1OH, CH—(CH$_3$)$_2$+CH(OH)—CH$_2$—CH(OH); 2.45 (m, 4H, CH$_2$—COOCH$_3$); 3.18 (d, 2H, OH); 3.62 (d, 2H, OH); 3.7 (s, 6H, COOCH$_3$); 4.13 (m, 2H, CH—OH); 4.38 (m, 2H, CH—CH); 4.7 (m, 2H, CH(CH$_3$)$_2$); 5.32 (dd, 2H, Olefin-H); 6.1 (d, 2H, Olefin-H); 6.85 (m, 4H, 3—H); 7.0 (m, 4H, 2—H).

EXAMPLE 9

Disodium 3,4-bis-(4-fluorophenyl)-1-isopropyl-2,5-pyrrole-bis-(3,5-dihydroxy-hept-6-enoate)

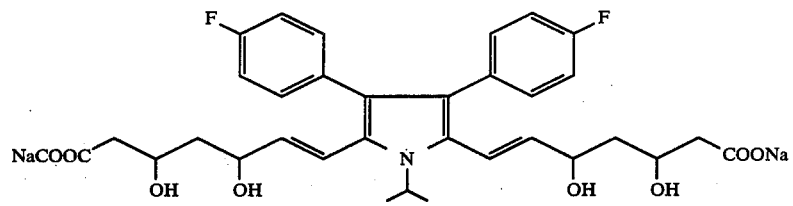

86 mg (0.13 mmol) of the compound from Example 8 are stirred for 1.5 hours at room temperature in 2 ml of tetrahydrofuran with 0.25 ml of 1M aqueous sodium hydroxide solution. The reaction mixture is concentrated on a rotary evaporator and dried over phosphorus pentoxide in a high vacuum.

Yield: 72 mg (81% of theory) of amorphous yellowish solid.

Dec. from 200° C.

$^1$H-NMR (CD$_3$OD): $\delta = 1.25$–1.6 (m, 1OH, CH—(CH$_3$)$_2$+CH(OH)CH$_2$—CH(OH)); 2.25 (m, 4H, CH$_2$—COOCH$_3$); 3.85 (m, 2H, CH—OH); 4.25 (m, 2H, CH—OH); 5.35 (m, 2H, Olefin-H); 6.6 (d, 2H, Olefin-H); 6.8–7.1 (m, 8H, Aromatic H).

EXAMPLE 10

Sodium 4-cyano-3,4-bis(4-fluorophenyl)-3H-4,5-dihydropyrrole-2-carboxylate

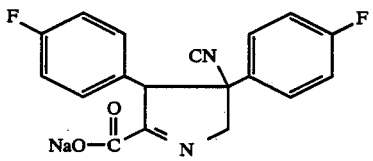

A warm solution of 62 g (0.55 mol) of ethyl isocyanoacetate and 101 g (0.42 mol) of the compound from Example 1 in 50 ml of dimethyl sulphoxide and 450 ml of tetrahydrofuran is added dropwise at $-15°$ C. to a suspension of 17.7 g (0.59 mol) of 80% strength sodium hydride in 450 ml of anhydrous tetrahydrofuran and the mixture is stirred for 1 hour at $-15°$ C. 500 ml of water are cautiously added dropwise at this temperature, then the mixture is allowed to warm to room temperature with stirring. It is extracted four times using ethyl acetate and the organic phases are rejected. A voluminous slightly colored precipitate, which is filtered off with suction and dried over phosphorus pentoxide in vacuo, deposits from the aqueous phase.

Yield 95 g (62%). By recrystallization from water, colorless crystals are obtained which decompose at 193°–194° C., then become solid and melt again at 252°–253° C. with decomposition.

| C$_{18}$H$_{11}$F$_2$NaNO$_3$.H$_2$O (366.3) | | | | |
|---|---|---|---|---|
| C | H | F | Na | N |
| Cal. 59.0 | 3.6 | 10.4 | 6.3 | 7.6 |
| Found 58.0 | 3.3 | 10.5 | 6.0 | 7.5 |
| $^1$H—NMR (D$_6$-DMSO: = 4.5 (m, 2H, CH$_2$) | | | | |
| 4.7 (s, 1H, 3-H) | | | | |
| 7.1–7.9 (m, 8H, Ar—H) | | | | |

EXAMPLE 11

3,4-Bis-(4-fluorophenyl)-pyrrole

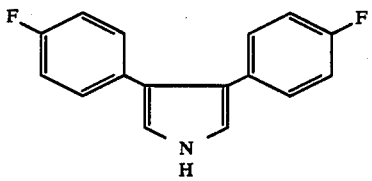

1.63 g (4.45 mmol) of the compound from Example 10 and 3 g of ethanolamine are heated at 100° C. for 3 h. 50 g of ice water is added to the solution and the mixture is extracted three times using ethyl acetate. The combined org. phases are washed with 1N hydrochloric acid, saturated bicarbonate solution and saturated sodium chloride mixture, dried over sodium sulphate and concentrated. The residue (1.7 g of brown oil) is filtered over 50 g of silica gel using petroleum ether/methylene chloride (2:1). Yield: 0.77 g (68% of theory) of slightly colored crystals of melting point 142° C.

USE EXAMPLE

EXAMPLE 12

The determination of enzyme activity was carried out as modified by G. C. Ness et al., Archives of Biochemistry and Biophysics 197, 493–499 (1979). Male Rico rats (body weight 300–400 g) were treated for 11 days with Altromin powdered feed to which 40 g of cholestyramine/kg of feed were added. After decapitation, the liver was removed from the animals and placed on ice. The livers were comminuted and homogenized in a homogenizer 3 times in 3 volumes of 0.1 m saccharose, 0.05 m KCl, 0.04 m K$_x$H$_y$ phosphate (mixture of K$_2$HPO$_4$ and KH$_2$PO$_4$ having pH 7.2), 0.03 m ethylenediaminetetraaceti acid, 0.002 m dithiothreitol (SPE) buffer (saccharose-phosphate-ethylenediaminetetraacetic acid buffer) at pH 7.2. The mixture was subsequently centrifuged for 15 minutes and the sediment was rejected. The supernatant was sedimented for 75 minutes. The pellet is taken up in ¼ volumes of SPE buffer, homogenized again and subsequently centrifuged again for 60 minutes. The pellet is taken up using a 5-fold amount of its volume of SPE buffer, homogenized and frozen and stored at $-78°$ C. (=enzyme solution).

For testing, the test compounds (or mevinolin as reference substance) were dissolved in dimethylformamide with the addition of 5% by volume of 1N NaOH and employed in various concentrations in the enzyme test using 10 $\mu$l. The test was started after 20 minutes preincubation of the compounds with the enzyme at 37° C. The test batch was 0.380 mol and contained 4 $\mu$mol of glucose-6-phosphate, 1.1 mg of bovine serum albumin, 1.2 $\mu$mol of dithiothreitol, 0.35 $\mu$mol of NADP, 1 unit of glucose-6-phosphate dehydrogenase, 35 $\mu$mol of K$_x$H$_y$ phosphate pH 7.2, 20 $\mu$l of enzyme preparation and 56 nmol of 3-hydroxy-3-methyl-glutaryl coenzyme A (glutaryl-3-$^{14}$C) 100,000 dpm.

The batch was incubated at 37° C. for 60 minutes and the reaction was stopped by the addition of 300 $\mu$l of 0.24 m HCl. After a post-incubation of 60 minutes at 37° C., the batch was centrifuged and 600 $\mu$l of the supernatant was applied to a 0.7×4 cm column filled with 5-chloride anion exchanger with a grain size of 100–200 mesh (anion exchanger). The column was washed with 2 ml of distilled water and 3 ml of a scintillation fluid were added to runnings plus washing water and counted in a scintillation counter. IC$_{50}$ values were determined by intrapolation by plotting the percentage inhibition against the concentration of the compound in the test. To determine the relative inhibitory potency, the IC$_{50}$ value of the reference substance mevinolin was set at 1 and compared with the simultaneously determined IC$_{50}$ value of the test compound.

This shows that the active compound according to the invention show a higher action than mevinolin.

For example the relative acitvity of compound of Example 9 is 40 (compared with mevinolin=1).

EXAMPLE 13

The subchronic action of the compounds according to the invention on the blood cholesterol values of dogs was examined in feeding experiments of several weeks duration. To this end, the substance to be investigated was given p.o. once daily in a capsule to healthy beagle dogs together with the feed over a period of several weeks. Colestyramine (4 g/100 g of feed) as the gallic acid sequestrant was additionally mixed with the feed during the entire experimental period, i.e. before, during and after the administration period of the substance to be investigated. Twice weekly, venous blood was taken from the dogs and the serum cholesterol was determined enzymatically. The serum chloesterol values during the administration period were compared with the serum cholesterol values before the administration period (control).

It is understood that the specification and examples are illustrative but not limitative of the present invention and that other embodiments within the spirit and scope of the invention will suggest themselves to those skilled in the art.

I claim:

1. A disubstituted pyrrole of the formula

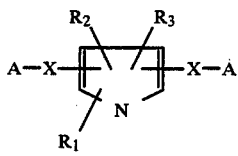

in which $R^1$
- denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by fluorine, chlorine, bromine, lower alkyl, lower alkoxy, phenyl, phenoxy, trifluoromethyl, trifluoromethoxy or lower alkoxycarbonyl, each of which is identical or different, or
- denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —$NR^4R^5$, each of which is identical or different, $R^2$
- denotes cyclopropyl, cyclopentyl or cyclohexyl, or
- denotes lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl or lower alkylcarbonyl, or by a group of the formula —$NR^4R^5$, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heterocyclic and aryl radicals mentioned can be monosubstituted or disubstituted by fluorine, chlorine, bromine, lower alkyl, lower alkoxy, trifluoromethyl or trifluoromethoxy, each of which is identical or different, $R^3$
- denotes hydrogen, or
- denotes cyclopropyl, cyclopentyl or cyclohexyl, or
- denotes lower alkyl which can be substituted by fluorine, chlorine, bromine, cyano, lower alkoxy, lower alkylthio, lower alkylsulphonyl, trifluoromethyl, trifluoromethoxy, trifluoromethylsulphonyl, lower alkoxycarbonyl, benzoyl, lower alkylcarbonyl or by a group of the formula —$NR^4R^5$, or by pyridyl, pyrimidyl, pyrazinyl, pyridazinyl, quinolyl, isoquinolyl, pyrrolyl, indolyl, thienyl, furyl, imidazolyl, oxazolyl, thiazolyl, phenyl, phenoxy, phenylthio, phenylsulphonyl, benzyloxy, benzylthio, benzylsulphonyl, phenylethoxy, phenylethylthio or phenylethylsulphonyl, where the heterocyclic and aryl radicals mentioned can be monosubstituted or disubstituted by fluorine, chlorine, bromine, lower alkyl, lower alkoxy, trifluoromethyl or trifluoromethoxy, each of which is identical or different,
- denotes thienyl, furyl, thiazolyl, isothiazolyl, oxazolyl, isoxazolyl, pyridyl, pyrimidyl, pyrazinyl, pyridazinyl, indolyl, isoindolyl, quinolyl, isoquinolyl, phthalazinyl, quinoxalinyl, quinazolinyl, cinnolinyl, benzothiazolyl, benzoxazolyl or benzimidazolyl, each of which can be monosubstituted or disubstituted by fluorine, chlorine, bromine, lower alkyl, lower alkoxy, phenyl, phenoxy, trifluoromethyl, trifluoromethoxy or lower alkoxycarbonyl, each of which is identical or different, or
- denotes phenyl or naphthyl, each of which can be monosubstituted to tetrasubstituted by lower alkyl, lower alkoxy, lower alkylthio, lower alkylsulphonyl, phenyl, phenyloxy, phenylthio, phenylsulphonyl, benzyl, benzyloxy, benzylthio, benzylsulphonyl, phenethyl, phenylethoxy, phenylethylthio, phenylethylsulphonyl, fluorine, chlorine, bromine, cyano, trifluoromethyl, trifluoromethoxy, trifluoromethylthio or lower alkoxycarbonyl, or by a group of the formula —$NR^4R^5$, each of which is identical or different, where
$R^4$ and $R^5$ are identical or different and denote lower alkyl, phenyl, benzyl, acetyl, benzoyl, phenylsulphonyl or lower alkylsulphonyl, X denotes a group of the formula $CH_3$—$CH_2$— or —CH=CH— and

A denotes a group of the formula

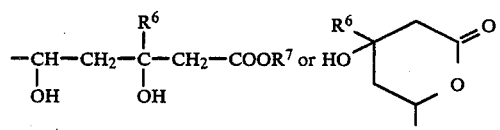

wherein
R⁶
denotes hydrogen or lower alkyl,
and
R⁷
denotes a $C_1$ to $C_6$ alkyl radical, a $C_6$ to $C_{12}$ aryl radical or a $C_7$ to $C_{10}$ aralkyl radical, or
denotes a physiologically tolerable cation.

2. A composition for inhibiting 3-hydroxy-3-methylglutaryl coenzyme A and cholesterol biosynthesis comprising an amount effective therefor of a compound according to claim 1 and a diluent.

3. A disubstituted pyrrole according to claim 1, in which
R¹
denotes pyridyl, pyrimidyl, quinolyl or isoquinolyl, each of which can be substituted by fluorine, chlorine, methyl, methoxy or trifluoromethyl, or
denotes phenyl which can be monosubstituted, disubstituted or trisubstituted by methyl, ethyl, propyl, isopropyl, butyl, isobutyl, tert.butyl, methoxy, ethoxy, propoxy, isopropoxy, butoxy, isobutoxy, tert.butoxy, methylthio, ethylthio, propylthio, isopropylthio, methylsulphonyl, ethylsulphonyl, propylsulphonyl, isopropylsulphonyl, phenyl, phenoxy, benzyl, benzyloxy, fluorine, chlorine, bromine, cyano, trifluoromethyl, trifluoromethoxy, methoxycarbonyl, ethoxycarbonyl, propoxycarbonyl, isopropoxycarbonyl, butoxycarbonyl, isobutoxycarbonyl or tertbutoxycarbonyl, each of which is identical or different,
R²
denotes cyclopropyl, cyclopentyl or cyclohexyl, or
denotes methyl, ethyl, propyl, isopropyl, butyl, sec.-butyl or tert.butyl, each of which can be substituted by fluorine, chlorine, bromine, cyano, methoxy, ethoxy, propoxy, isopropoxy, butoxy, sec.butoxy, tert.butoxy, methylthio, ethylthio, propylthio, isopropylthio, methylsulphonyl, ethylsulphonyl, propylsulphonyl, isopropylsulphonyl, trifluoromethyl, trifluoromethoxy, methoxycarbonyl, ethoxycarbonyl, butoxycarbonyl, isobutoxycarbonyl, tert.-butoxycarbonyl, benzoyl, acetyl, pyridyl, pyrimidyl, thienyl, furyl, phenyl, phenoxy, phenylthio, phenylsulphonyl, benzyloxy, benzylthio or benzylsulphonyl,
R³
denotes hydrogen, cyclopropyl, cyclopentyl or cyclohexyl, or
denotes methyl, ethyl, propyl, isopropyl, butyl, isobutyl, tert.butyl, pentyl, isopentyl, hexyl or isohexyl, each of which can be substituted by fluorine, chlorine, bromine, cyano, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, trifluoromethyl, trifluoromethoxy, methoxycarbonyl, ethoxycarbonyl, propoxycarbonyl, isopropoxycarbonyl, butoxycarbonyl, isobutoxycarbonyl, tert.butoxycarbonyl, benzoyl, acetyl or ethylcarbonyl, or by a group —NR⁴R⁵, or by pyridyl, pyrimidyl, pyrazinyl, pyridazinyl, quinolyl, isoquinolyl, thienyl, furyl, phenyl, phenoxy, phenylthio, phenylsulphonyl, benzyloxy, benzylthio or benzylsulphonyl, where the heteroaryl and aryl radicals mentioned can be substituted by fluorine, chlorine, methyl, ethyl, propyl, isopropyl, isobutyl, tert.butyl, methoxy, ethoxy, propoxy, isopropoxy, butoxy, isobutoxy, tert.-butoxy, trifluoromethyl or trifluoromethoxy, or
denotes thienyl, furyl, pyridyl, pyrimidyl, pyrazinyl, pyridazinyl, oxazolyl, isooxazolyl, imidazolyl, pyrazolyl, thiazolyl, isothiazolyl, quinolyl, isoquinolyl, benzoxazolyl, benzimidazolyl or benzothiazolyl, where the radicals mentioned can be substituted by fluorine, chlorine, methyl, ethyl, propyl, isopropyl, butyl, isobutyl, tert.-butyl, methoxy, ethoxy, propoxy, isopropoxy, butoxy, isobutoxy, tert.butoxy, phenyl, phenoxy, trifluoromethyl, trifluoromethoxy, methoxycarbonyl, ethoxycarbonyl, isopropoxycarbonyl, propoxycarbonyl, butoxycarbonyl, isobutoxycarbonyl or tert.butoxycarbonyl, or
denotes phenyl which can be monosubstituted, disubstituted or trisubstituted by methyl, ethyl, propyl, isopropyl, butyl, isobutyl, tert.butyl, pentyl, isopentyl, hexyl, isohexyl, methoxy, ethoxy, propoxy, isopropoxy, butoxy, isobutoxy, tert.butoxy, methylthio, ethylthio, propylthio, isopropylthio, butylthio, isobutylthio, tert.butylthio, methylsulphonyl, ethylsulphonyl, propylsulphonyl, isopropylsulphonyl, butylsulphonyl, isobutylsulphonyl, tert.butylsulphonyl, phenyl, phenoxy, phenylthio, phenylsulphonyl, benzyl, benzyloxy, benzylthio, benzylsulphonyl, fluorine, chlorine, bromine, cyano, trifluoromethyl, trifluoromethoxy, trifluoromethylthio, methoxycarbonyl, ethoxycarbonyl, propoxycarbonyl, isopropoxycarbonyl, butoxycarbonyl, isobutoxycarbonyl or tert.butoxycarbonyl, or by a group —NR⁴R⁵, each of which is identical or different,
wherein
R⁴ and R⁵ are identical or different and denote methyl, ethyl, propyl, isopropyl, butyl, isobutyl, tert.butyl, phenyl, benzyl, acetyl, methylsulphonyl, ethylsulphonyl, propylsulphonyl, isopropylsulphonyl or phenylsulphonyl,
X denotes a group of the formula —CH=CH—
and
A denotes a group of the formula

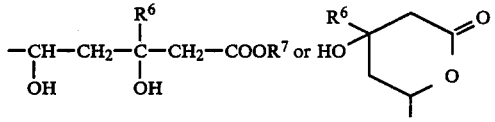

wherein
R⁶
denotes hydrogen, methyl, ethyl, propyl, isopropyl, butyl, isobutyl or tert.butyl
and
R⁷
denotes hydrogen, methyl, ethyl, propyl, isopropyl, butyl, isobutyl, tert.butyl or benzyl, or
denotes a sodium, potassium, calcium or magnesium or ammonium ion.

4. A disubstituted pyrrole according to claim 1, in which
R¹ denotes phenyl which can be monosubstituted or disubstituted by methyl, phenoxy, fluorine or trifluoromethyl, each of which is identical or different, R$^2$
  denotes isopropyl, cyclopropyl or tert.butyl, R$^3$
  denotes cyclopropyl, isopropyl, tert.-butyl or phenyl, each of which can be monosubstituted or disubstituted by fluorine, methyl, phenoxy or trifluoromethyl, each of which is identical or different, X denotes a group of the formula

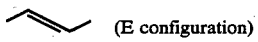 (E configuration)

and

A denotes a group of the formula

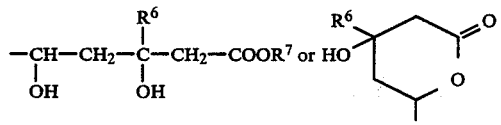

wherein
R$^6$
  denotes hydrogen
and
R$^7$
  denotes hydrogen, methyl or ethyl, or
  denotes a sodium or potassium cation.

5. A compound according to claim 1, wherein such compound is 3,4-bis-(4-fluorophenyl)-2,5-bis-(3,5-dihydroxy-6-carboxy-hex-1-enyl)-1-isopropyl-pyrrole of the formula

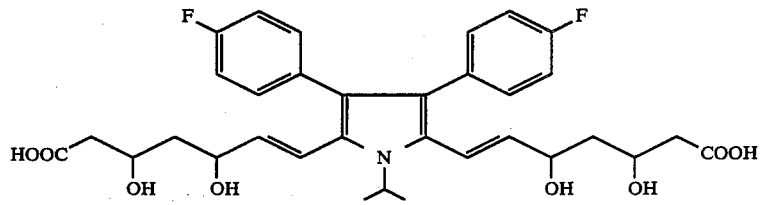

or an alkyl ester or salt thereof.

6. A compound according to claim 5, in the form of the dimethyl ester thereof.

7. A compound according to claim 5, in the form of the disodium salt thereof.

8. A method of inhibiting 3-hydroxy-3-methylglutaryl coenzyme A and cholesterol biosynthesis in a patient in need thereof which comprises administering to such patient an amount effective therefor of a compound according to claim 1.

9. A unit dose of a composition according to claim 2 in the form of a tablet, capsule or ampule.

10. The method according to claim 8, wherein such compound is the dimethyl ester or di-sodium salt of 3,4-bis-(4-fluorophenyl)-2,5-bis-(3,5-dihydroxy-6-carboxy-hex-1-enyl)-1-isopropyl-pyrrole.

* * * * *

UNITED STATES PATENT AND TRADEMARK OFFICE
CERTIFICATE OF CORRECTION

PATENT NO. : 4,937,255
DATED : June 26, 1990
INVENTOR(S) : Walter Hübsch, et al

It is certified that error appears in the above-identified patent and that said Letters Patent is hereby corrected as shown below:

Col. 36, line 58      Delete "$CH_3$" and substitute --$CH_2$--

Signed and Sealed this

Nineteenth Day of May, 1992

Attest:

DOUGLAS B. COMER

*Attesting Officer*      *Acting Commissioner of Patents and Trademarks*